(12) United States Patent
Wise et al.

(10) Patent No.: US 7,790,493 B2
(45) Date of Patent: Sep. 7, 2010

(54) WAFER-LEVEL, POLYMER-BASED ENCAPSULATION FOR MICROSTRUCTURE DEVICES

(75) Inventors: Kensall D. Wise, Ann Arbor, MI (US); Mayurachat Ning Gulari, Ann Arbor, MI (US); Ying Yao, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1044 days.

(21) Appl. No.: 11/440,983

(22) Filed: May 25, 2006

(65) Prior Publication Data

US 2007/0007240 A1 Jan. 11, 2007

Related U.S. Application Data

(60) Provisional application No. 60/684,596, filed on May 25, 2005.

(51) Int. Cl.
*H01L 21/00* (2006.01)

(52) U.S. Cl. .............. 438/52; 438/83; 438/98; 438/753; 257/E21.215; 257/E21.219; 257/E21.22

(58) Field of Classification Search .......... 438/51, 438/52, 53, 1, 705, 753, 83, 98, 99; 257/E21.309, 257/E21.215, E21.219, E21.22
See application file for complete search history.

(56) References Cited

U.S. PATENT DOCUMENTS

| | | | |
|---|---|---|---|
| 4,587,719 A | * | 5/1986 | Barth ................. 438/113 |
| 4,734,300 A | | 3/1988 | Simanyi et al. |
| 5,013,396 A | * | 5/1991 | Wise et al. ................ 438/51 |
| 5,332,469 A | | 7/1994 | Mastrangelo |
| 5,622,898 A | | 4/1997 | Zechman |
| 5,656,830 A | | 8/1997 | Zechman |
| 5,828,132 A | | 10/1998 | Eissa |
| 5,847,280 A | | 12/1998 | Sherman et al. |
| 6,511,859 B1 | | 1/2003 | Jiang et al. |
| 6,650,806 B2 | | 11/2003 | Rodgers et al. |
| 2002/0086446 A1 | | 7/2002 | Carpentier et al. |

(Continued)

OTHER PUBLICATIONS

Wise et al., Wireless Implantable Microsystems: High-Density Electronic Interfaces to the Nervous System, Proceedings of the IEEE, vol. 92, No. 1, Jan. 2004.*

(Continued)

*Primary Examiner*—Julio J Maldonado
(74) *Attorney, Agent, or Firm*—Marshall, Gerstein & Borun LLP

(57) ABSTRACT

Disclosed herein is a method of fabricating a device having a microstructure. The method includes forming a connector on a semiconductor substrate, coating the connector with a polymer layer, and immersing the semiconductor substrate and the coated connector in an etchant solution to form the microstructure from the semiconductor substrate and to release the coated connector and the microstructure from the semiconductor substrate such that the microstructure remains coupled to a further element of the device via the coated connector. In some cases, the microstructure is defined by forming an etch stop in the semiconductor substrate, and the microstructure and the semiconductor substrate are coated with a polymer layer, which may then be selectively patterned. The microstructure may then be released from the semiconductor substrate in accordance with the etch stop.

27 Claims, 14 Drawing Sheets

U.S. PATENT DOCUMENTS

| | | | |
|---|---|---|---|
| 2005/0107742 A1 | 5/2005 | Ghovanloo et al. | |
| 2006/0003090 A1 | 1/2006 | Rodger et al. | |
| 2007/0072330 A1* | 3/2007 | Popa et al. | 438/53 |
| 2007/0177287 A1* | 8/2007 | Oka et al. | 359/872 |

OTHER PUBLICATIONS

Akamatsu et al., "Fabrication and Evaluation of a Silicon Probe Array on a Flexible Substrate for Neural Recording," *Proc. of the 25th Annual Int'l Conf. of the IEEE EMBS*, pp. 3802-3805 (2003).

Fujitsuka et al., "Silicon Anisotropic Etching without Attacking Aluminum with Si and Oxidizing Agent Dissolved in TMAH Solution," *Transducers*, pp. 1667-1670 (2003).

Hetke et al., "3-D Silicon Probe Array with Hybrid Polymer Interconnect for Chronic Cortical Recording," *Proc. of the 1st Int'l IEEE EMBS Conf. on Neural Engineering*, pp. 181-184 (2003).

Hetke et al., "Silicon Ribbon Cables for Chronically Implantable Microelectrode Arrays," *IEEE Transactions on Biomedical Engineering*, vol. 41, No. 4, pp. 314-321 (1994).

Holman et al., "Silicon Micro-Needles with Flexible Interconnections," *Microtechnologies in Medicine & Biology 2nd Annual Int'l IEEE-EMBS Conf.*, pp. 255-260 (2002).

Kim et al., "A 64-Site Multishank CMOS Low-Profile Neural Stimulating Probe," *IEEE Journal of Solid-State Circuits*, vol. 31, No. 9, pp. 1230-1238 (1996).

Lian et al., "Characterisation of Aluminium Passivation for TMAH Based Anisotropic Etching for MEMS Applications," *Proc. of the 2000 Int'l Conf. on Microelectronic Test Structures*, pp. 210-214 (2000).

Liger et al., "Robust Parylene-to-Silicon Mechanical Anchoring", *IEEE 16th Annual Int'l Conf. on MEMS*, pp. 602-605 (2003).

Lisby et al., "Mechanical Characterization and Design of Flexible Silicon Microstructures," *J. Microelectromechanical Systems.*, vol. 13, No. 3, pp. 452-464 (2004).

Moon et al., "Buckling Strength of Coated and Uncoated Silicon Microelectrodes," *Proc. of the 25th Annual Int'l Conf. of the IEEE EMBS*, vol. 2, pp. 1944-1947 (2003).

Norlin et al., "A 32-site Neural Recording Probe Fabricated by DRIE of SOI Substrates," *J. Micromechanics and Microeng.*, vol. 12, pp. 414-419 (2002).

Pang et al., "A New Multi-Site Probe Array with Monolithically Integrated Parylene Flexible Cable for Neural Prostheses," *Proc. of 27th Annual Int'l Conf. of the Engineering in Medicine and Biology Society*, pp. 7114-7117 (Sep. 2005).

Sonphao et al., "Silicon Anisotropic Etching of TMAH Solution," *IEEE Int'l Symposium on Industrial Electronics*, pp. 2049-2052 (2001).

Suzuki et al., "A 3D Flexible Parylene Probe Array for Multichannel Neural Recording," *Proc. of the 1st Int'l IEEE EMBS Conf. on Neural Engineering*, pp. 154-156 (2003).

Takeuchi et al., "3D Flexible Multichannel Neural Probe Array," *J. Micromechanics and Microeng.*, vol. 14, pp. 104-107 (2004).

Ucok et al., "Modular Assembly/Packaging of Multi-Substrate Microsystems (WIMS CUBE) Using Thermo-Magnetically Actuated Cables," *18th IEEE Int'l Conf. on MEMS*, pp. 536-539 (2005).

Weiland et al., "Recessed Electrodes Formed by Laser Ablation of Parylene Coated, Micromachined Silicon Probes," *Proc. of the 19th Annual Int'l Conf of the IEEE Engineering in Medicine and Biology Society*, vol. 5, pp. 2273-2276 (1997).

Wise et al., "Wireless Implantable Microsystems: High-Density Electronic Interfaces to the Nervous System," *Proceedings of the IEEE*, vol. 92, No. 1, pp. 76-97 (2004).

Yan et al., "An Improved TMAH Si-etching Solution without Attacking Exposed Aluminum," *Proc. of the IEEE Micro Electro Mechanical Systems*, pp. 562-567 (2000).

Yao et al. "A Low-Profile Three-Dimensional Silicon/Parylene Stimulating Electrode Array for Neural Prosthesis Applications," *Proc. of 27th Annual Int'l Conf. of the Engineering in Medicine and Biology Society*, pp. 1293-1296 (Sep. 2005).

International Search Report from PCT/US06/20532.

International Preliminary Report on Patentability from PCT/US06/20532.

\* cited by examiner

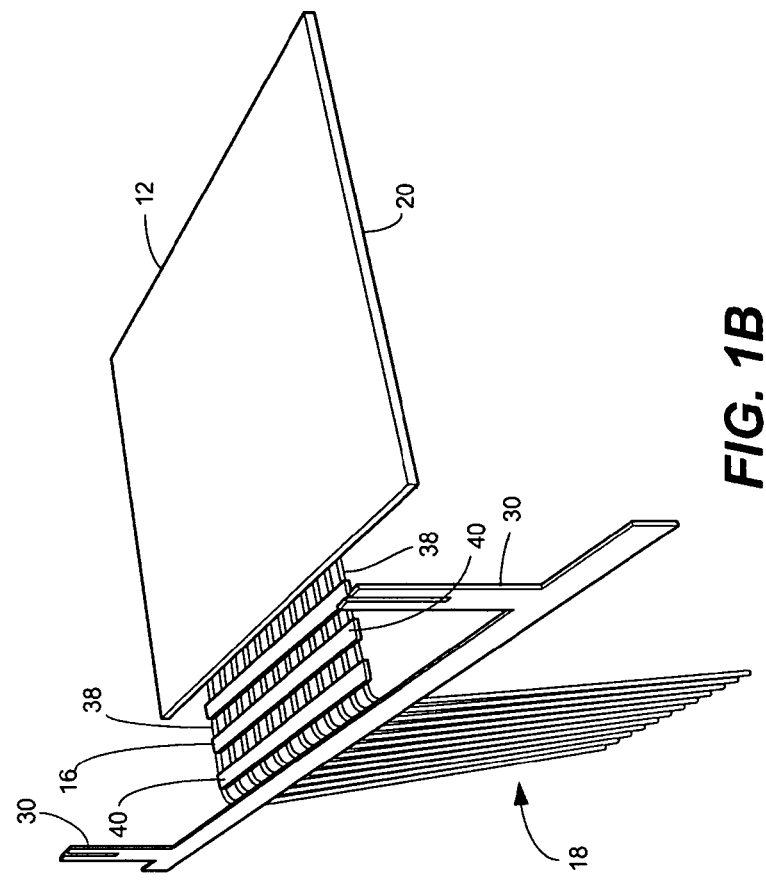
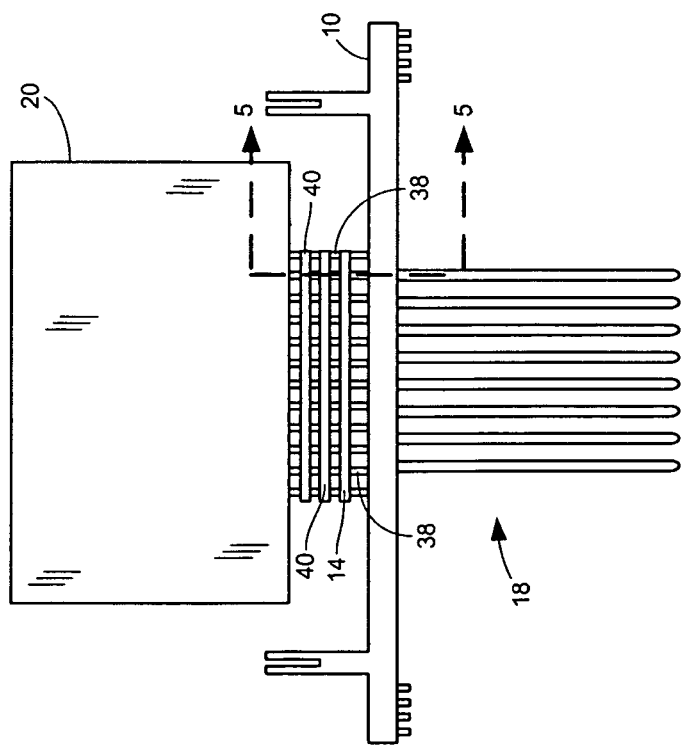
FIG. 1B
FIG. 1A

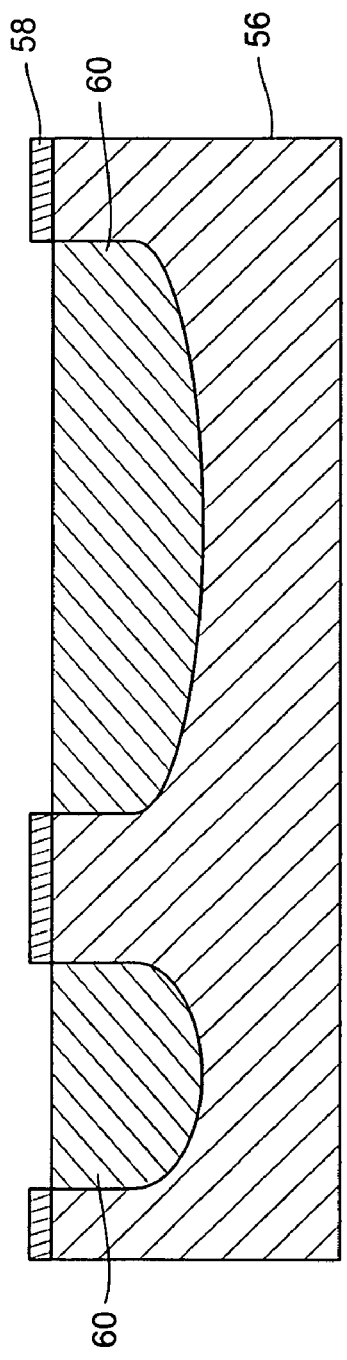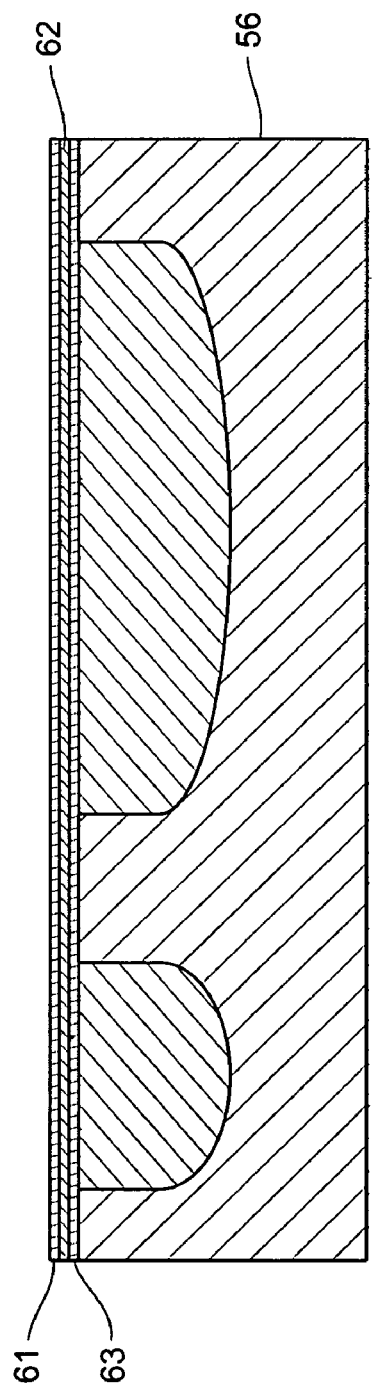

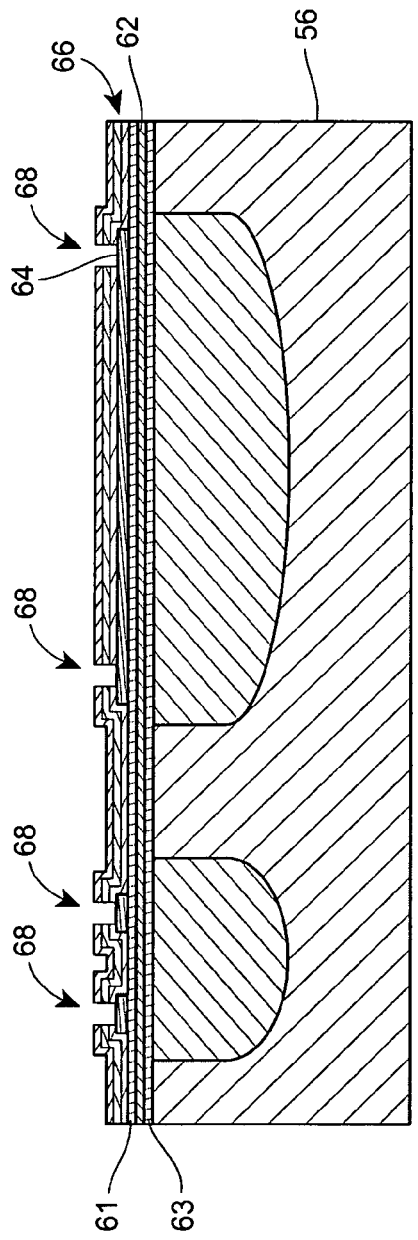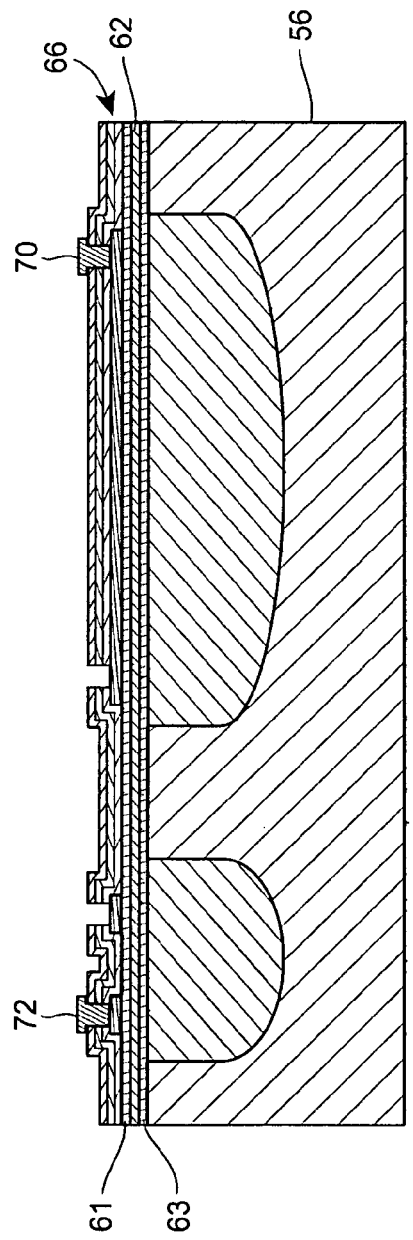

WAFER-LEVEL, POLYMER-BASED ENCAPSULATION FOR MICROSTRUCTURE DEVICES

CROSS-REFERENCE TO RELATED APPLICATION

This application claims the benefit of U.S. provisional application entitled "Integrated Silicon/Polymer Devices and Fabrication Process for Neural and Other Applications," filed May 25, 2005, and having Ser. No. 60/684,596, the entire disclosure of which is hereby expressly incorporated by reference.

STATEMENT REGARDING FEDERALLY SPONSORED RESEARCH OR DEVELOPMENT

This invention was made with government support under Contracts Nos.: EEC-9986866 and N01-NS-4-2363 awarded by National Science Foundation and the National Institute of Health, respectively. The government has certain rights in the invention.

BACKGROUND OF THE DISCLOSURE

1. Field of the Disclosure

The disclosure relates generally to micromachined devices and, more particularly, to batch fabrication of micromachined devices with integrated polymer coating.

2. Brief Description of Related Technology

Advances in neural prostheses have been based on the development of microelectrodes directed to producing high fidelity sensation and selectively controlling the activity of neural ensembles. Silicon micromachined electrodes have been under development for many years, progressing from 2D passive probes to a variety of two-dimensional and three-dimensional active devices with integrated circuitry incorporated on-chip.

Such devices are also in wide use today for studying the nervous system. A rational map between each sensory or motor function and a corresponding region in the cerebral cortex is thought to exist. Electrical stimulation and recording techniques for the central nervous system have been investigated to study and eventually restore neurological or physiological functions, such as the sensations of sound and light. To these ends, the microelectrodes have been surgically implanted into tissue near target neurons for delivery of small currents or measurement of the extracellular action potentials from neural discharges. Early electrodes were made from insulated metal wires and glass micropipettes, and remain widely used.

Advances in neuroscience and neuroprosthetics have driven the development of more complex devices, such as multi-channel microelectrodes capable of accessing many different neurons simultaneously with good spatial resolution. Since the late 1960's, microelectronic thin-film techniques traditionally used to fabricate semiconductor devices have been utilized for this application to develop dense electrode arrays. Such microfabrication techniques have several potential technological advantages, including a high degree of reproducibility and precise control of the spatial positions of the electrode sites.

Recent work has been directed to fabricating thin-film electrodes in a silicon microelectrode array. As the traditional material used in semiconductor industry, silicon has been intensively characterized both electrically and mechanically. Selectively-diffused boron has thus been used as an etch stop to specify the thickness of the probes, or shanks, upon which the electrodes are disposed. The definition of the microelectrode arrays has thus relied upon the different wet etch rates (~100:1) for silicon and boron-doped silicon with anisotropic silicon etchants, such as ethylene diamine pyrocatechol (EDP). Past silicon microelectrode devices have typically consisted of a silicon backend for handling and sharp penetrating shanks to insert into the neural tissue. Polysilicon or aluminum has been used for interconnects encapsulated by dielectric stacks of $SiO_2/Si_3N_4/SiO_2$. CMOS circuitry has been integrated into the silicon backend for control and signal processing functionality.

The thickness of the dielectric stacks has been adjusted for stress compensation to control stress-induced curvature. For intracortical applications, the probes are straight to facilitate penetration into the pia membrane. For cochlear implants, the probes are curled for easy insertion into the cochlea. After the deposition and patterning steps for the stimulating/recording electrode sites, the probes are released from the silicon wafer via the above-described anisotropic etching. This fabrication technique allows arbitrary shapes of probes and electrode sites to be patterned with dimensions controlled to better than ±1 µm. The etch stop is configured such that the released probes have a thickness, often as small as 12 µm, capable of accommodating the buckling strength for tissue penetration in neural applications.

One of the primary obstacles to long-term implantation of these devices has been the absence of a satisfactory mechanism for connecting the electrodes to the outside world, let alone one compatible with the wet etch-based fabrication technique described above. In one past case, the interconnections in these devices were implemented with flexible silicon ribbon cables. See, e.g., Hetke et al., "Silicon Ribbon Cables for Chronically Implantable Microelectrode Arrays," *IEEE Transactions on Biomedical Engineering*, Vol. 41, No. 4, pp. 314-321 (1994). In this technique, a shallow boron diffusion is used to define a boron etch stop about 5 µm deep in the silicon substrate in order to fabricate the flexible silicon ribbon cable with conducting polysilicon interconnects insulated by the stacks of silicon dioxide and silicone nitride. The silicon ribbon cable extends from the microelectrodes to connect to a percutaneous plug in the skull for communication with an external control unit.

The same technique has been used for a foldable interconnecting structure for a low-profile probe. See Kim, et al., "A 64-Site Multishank CMOS Low-Profile Neural Stimulating Probe," *IEEE J. Solid-State Circuits*, Vol. 31, pp. 1230-1238 (1996). In order to allow the dura membrane to be replaced over the electrode so that it remains free of the skull in chronic implant situations, the vertical rise of the electrode above the cortical surface must be less than 1 mm for the human brain. Otherwise, skull regrowth will cause the implanted device to become anchored to the skull. As a result, the silicon backend supporting the CMOS circuitry has been folded down at a right angle to the penetrating shanks so that it lays flat on the cortical surface after implantation. The silicon ribbon cables have provided a flexible interconnection between these two silicon components.

These silicon ribbon-based interconnections, however, give rise to complications during use of the probes. With a Young's Modulus of about 107 GPa, silicon has sufficient buckling strength to penetrate the pia membrane for insertion into the neural tissue during device implantation. But silicon is a rigid solid material easily fractured under stresses, and structural flexibility in connection with the silicon microelectrode may involve bending to small radii without fracture and tethering.

In addition to their susceptibility to shear stress, silicon ribbon cables are very elastic and tend to spring back to their original state after being bent. As a result, the tethering associated with bending the cable after surgical insertion can cause dislocation of penetrating shanks from the original implant area and undesirable stress on the dura membrane on top of the implanted device.

Biocompatible polymers have also been incorporated into MEMS devices, including silicon microelectrode devices. The resulting devices are generally capable of significant deformation without fracturing, and therefore can better adjust to brain micromotion with less tethering to the neural tissue.

Unfortunately, polymer materials have exhibited a tendency to develop pinholes and become embrittled after exposure to silicon etching solutions under traditional conditions for device release. As a result, integrated silicon/polymer fabrication processes have generally not been explored. Instead, alternative methods have been employed, such as post-process polymer coating, using separate polymer structures to form a hybrid connection with silicon devices, or changing the process flow to use dry etch techniques. The former two methods disadvantageously require the handling of individual structures, while the latter cannot be applied in general cases.

One technique for forming polymer-coated microelectrode devices that was not suitable for batch fabrication, or wafer-level processing, involved rivet-bonding a flexible polyimide cable to individually released silicon probes. Hetke, et al., "3-D Silicon Probe Array with Hybrid Polymer Interconnect for Chronic Cortical Recording," *Conf. Proc. First Intl. IEEE EMBS Conference on Neural Engineering*, pp. 181-184 (2003). Another technique involved depositing a conformal polymer coating on the released silicon probes to form flexible structures. Drawbacks of this technique include the lack of polymer deposition selectivity and the difficulty in removing unwanted polymer coating on the electrodes. For example, laser ablation has been employed to remove the unwanted coating of iridium sites after parylene deposition. See Weiland, et al., "Recessed Electrodes Formed by Laser Ablation of Parylene Coated, Micromachined Silicon Probes," *Proc. of the 19th Annual Intl. Conf. of the IEEE Engineering in Medicine and Biology Society*, Vol. 5, pp. 2273-2276 (1997). Complications arise with parylene residue leftover in under-ablated regions or iridium damage in over-ablated areas. Another effort attempted to use discharge breakdown to remove a parylene coating on the silicon probes. Akamatsu, et al., "Fabrication and Evaluation of a Silicon Probe Array on a Flexible Substrate for Neural Recording," Proc. of the 25th Annual Intl. Conf. of the IEEE Engineering in Medicine and Biology Society, Vol. 4, pp. 3802-3805 (2003). However, the removal was undesirably limited only to the probe tips.

In each of these polymer-based techniques, post-fabrication processes required handling of individual probes. As a result, the use of polymer coatings would introduce dramatic inefficiencies once hundreds, if not thousands, of silicon probes are released from a silicon wafer.

SUMMARY OF THE DISCLOSURE

In accordance with one aspect of the disclosure, a method is useful for fabricating a device having a microstructure. The method includes the steps of forming a connector on a semiconductor substrate, coating the connector with a polymer layer, and immersing the semiconductor substrate and the coated connector in an etchant solution. The microstructure is thus formed from the semiconductor substrate, and the coated connector and the microstructure are released from the semiconductor substrate, such that the microstructure remains coupled to a further element of the device via the coated connector.

In some cases, the method further includes the step of defining the microstructure by forming an etch stop in the semiconductor substrate for the immersing step.

The connector forming step may include depositing a conductive layer such that the connector includes an interconnect between the microstructure and the further element of the device. The conductive layer may include gold. Alternatively, the conductive layer includes aluminum. The method may then further include the step of encapsulating the conductive layer with one or more dielectric layers before the coating step.

In some embodiments, the forming step includes the step of defining a plurality of connectors, each of which includes a serpentine-shaped region, and between each of which the etchant solution flows during the immersing step.

The method may also further include the step of defining a brace in the semiconductor substrate as an anchor for the polymer layer.

In some cases, the method may further include the step of encapsulating the connector with one or more dielectric layers before the coating step.

In some embodiments, the semiconductor substrate may be thinned before the immersing step via backside etching.

The coating step may include the steps of curing and treating the polymer layer before the immersing step.

The polymer layer may include a polymer selected from the group consisting of BCB, Parylene C, and Cytop.

The etchant solution may include TMAH. The etchant solution may include 10 wt. % TMAH solution and ammonium persulfate. The immersing step may then be performed at a temperature in a range of about 80 degrees Celsius to about 95 degrees Celsius.

In some embodiments, the coating step includes the steps of depositing the polymer layer on at least a portion of the microstructure, and selectively patterning the polymer layer before the immersing step.

In accordance with another aspect of the disclosure, a method of fabricating a device having a microstructure includes the steps of defining the microstructure by forming an etch stop in a semiconductor substrate, forming a connector on the semiconductor substrate, coating the connector with a polymer layer, and releasing the microstructure from the semiconductor substrate in accordance with the etch stop such that the microstructure remains coupled to a further element of the device via the coated connector.

In some cases, the connector forming step includes the step of defining a plurality of connectors, each of which comprises a serpentine-shaped region, and between each of which an etchant solution flows during the releasing step.

The method may further include the step of defining a brace in the semiconductor substrate as an anchor for the polymer layer.

The method may also further include the step of encapsulating the connector with one or more dielectric layers before the coating step.

In accordance with yet another aspect of the disclosure, a device includes a first device structure comprising a semiconductor platform, a second device structure comprising a microstructure spaced from the semiconductor platform, and a cable having a plurality of beams to couple the microstructure to the first device structure. Each beam of the plurality of beams has a polymer coating and a serpentine-shaped region.

In some cases, the device further includes a semiconductor brace crossing the plurality of beams to act as an anchor for the polymer coating.

The polymer coating may include a polymer selected from the group consisting of BCB, Parylene C, and Cytop.

In some embodiments, each beam includes a conductive layer such that the cable includes a plurality of interconnects between the microstructure and the first device structure. Each interconnect of the plurality of interconnects may include gold. Alternatively or additionally, each beam may be encapsulated by one or more dielectric layers under the polymer coating. In such cases, each interconnect of the plurality of interconnects may then include aluminum. The microstructure of the second device structure may also include a passivated conductive line and an exposed electrode site, where the passivated conductive line couples the exposed electrode site to one of the plurality of interconnects.

The polymer coating may include a polymer layer that extends over the length of the cable and over one or more of the first and second device structures.

In some cases, adjacent beams of the plurality of beams are spaced in parallel fashion.

In accordance with yet another aspect of the disclosure, a method of fabricating a device having a microstructure includes defining the microstructure by forming an etch stop in a semiconductor substrate, coating the microstructure and the semiconductor substrate with a polymer layer, selectively patterning the polymer layer, and releasing the microstructure from the semiconductor substrate in accordance with the etch stop after the polymer layer patterning step.

BRIEF DESCRIPTION OF THE DRAWING FIGURES

For a more complete understanding of the disclosure, reference should be made to the following detailed description and accompanying drawing figures, in which like reference numerals identify like elements in the figures, and in which:

FIGS. 1A and 1B are elevational and perspective schematic representations of exemplary microelectrode devices having polymer-coated connectors in accordance with one aspect of the disclosure, respectively;

FIGS. 5A-5K are cross-sectional views of the microelectrode device of FIG. 1A taken along line 5-5 in FIG. 1A during fabrication in accordance with another aspect of the disclosure;

Figure 2:
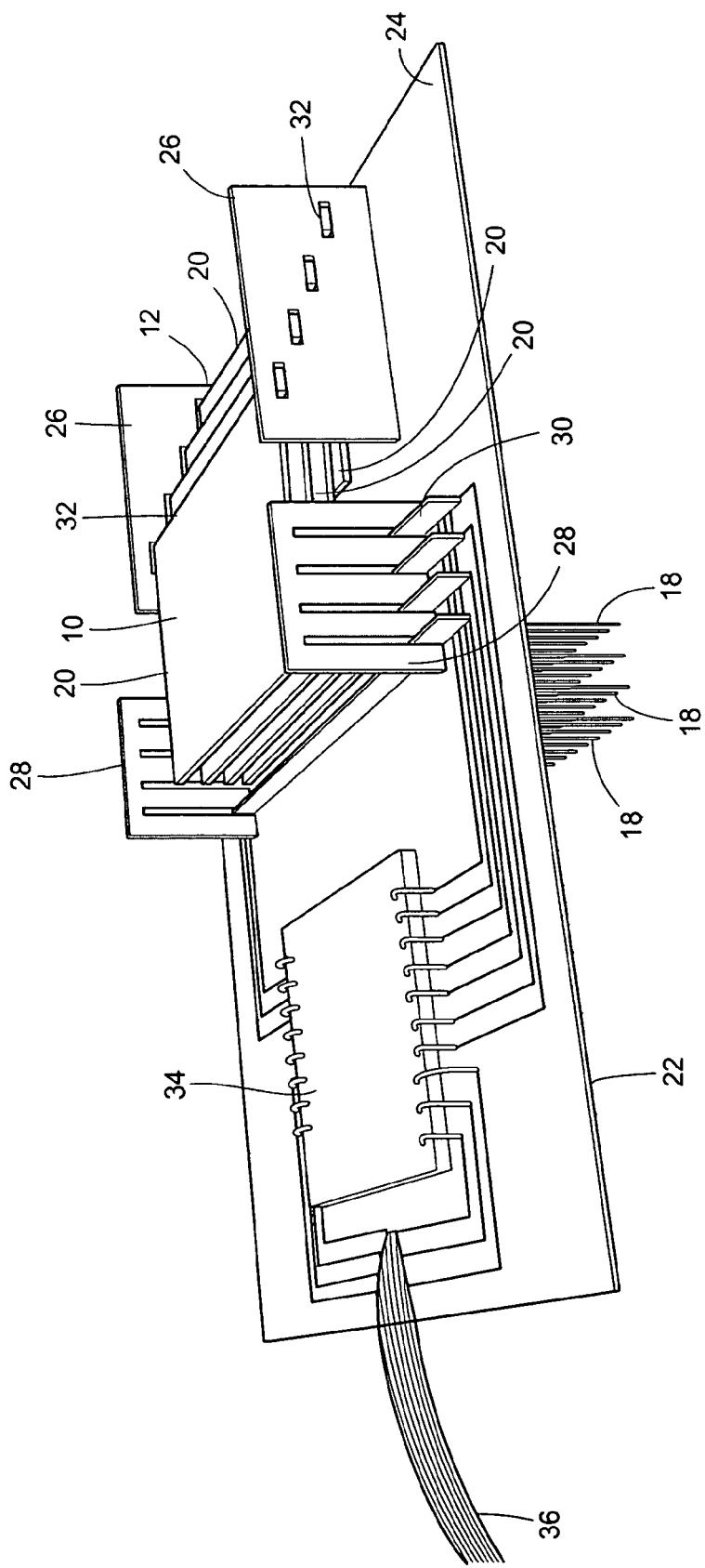
FIG. 2 is a schematic, perspective representation of a neural stimulating and recording device having a number of the microelectrode devices of either FIG. 1A or FIG. 1B.

While the disclosed methods and devices are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF PREFERRED EMBODIMENTS

Disclosed herein are microfabricated devices and microfabrication methods involving the integration of one or more polymer layers. The use of polymer layers for encapsulation and other purposes is made possible despite the use of wet etching release techniques, such as a dissolved wafer process (DWP). As a result, and as described below, the integration of the polymer layers with the semiconductor device structures formed via such techniques can be accomplished at the wafer level, via a batch fabrication technique that deposits and selectively patterns the polymer material before the device structure(s) are released from the wafer. Such wafer-level processing therefore avoids the complications and inefficiencies plaguing the polymer-based fabrication techniques that required individual device handling.

In some aspects, this disclosure relates to MEMS (microelectromechanical system) and other microfabricated devices with semiconductor (e.g., silicon) and polymer components suitable for use in biological applications. Biocompatible polymers include parylene, polyimide SU-8, cytop, and Benzocyclobutene (BCB). Exemplary applications include those related to neural system recording and stimulation.

Although disclosed in connection with, and well suited for use with, electrical stimulation and recording devices, the devices and methods disclosed herein are not limited to neural system recording and stimulation devices or other biological applications. On the contrary, the disclosed devices and methods are suitable for any number of applications involving flexible connections or cabling between device structures, including any type of microstructure or microfabricated device. Moreover, the disclosed devices and methods may also be applied in any context involving device encapsulation or coating with a polymer.

With the disclosed fabrication process, formerly inflexible silicon neural probes can be made more robust and flexible. In some embodiments, the process generally provides a polymeric connection between an implanted microelectrode array and the outside world using electrical and/or fluidic leads. Using the disclosed technique, silicon-based probes may be coated with a biocompatible polymer layer which is not prone to fracture and separation. The disclosed fabrication technique offers an ideal method for merging polymeric cables with silicon probes at the wafer level to provide structures which are robust enough for use in, for example, neural prostheses.

The integrated silicon/polymer process disclosed herein features batch fabrication and integrates polymer deposition and patterning into silicon fabrication on the wafer level before semiconductor wafer release. This avoids handling of individual structures, which helps to save time and expense in device development. In addition, post-fabrication processes may be minimized or totally eliminated with the potential of lowering the cost for packaging and increasing the lifetime and yield of the fabricated devices.

In some embodiments, the semiconductor wafer used in connection with the disclosed devices and methods is a silicon substrate. In addition to its biocompatibility, silicon supports the incorporation of integrated circuitry into the implanted electrodes to form a compact, active microsystem. For example, the disclosed fabrication techniques are compatible with a standard CMOS process to fabricate the circuitry. In some embodiments, such incorporation and integration reduces the overall size of the implanted device and simplifies the interfacial connection between the electrode(s) and the external control system while still allowing the use of many different sites. It is especially useful for the applications such as visual prostheses where thousands of electrode sites are necessary to elicit the sensation of light for basic pattern recognition.

Notwithstanding the foregoing advantages of silicon substrates, the following description is provided with the understanding that the microfabrication techniques and devices disclosed herein are not limited to any particular semiconductor substrate material, wafer type, or medium.

With reference now to the drawing figures, FIGS. 1A and 1B illustrate exemplary devices 10, 12 having flexible connectors 14, 16 in accordance with one aspect of the disclosure. In these cases, the connectors 14, 16 include one or more interconnects, i.e., conductive lines (not shown), for electrically coupling one device structure (or component) to another device structure (or component). More specifically, the exemplary devices may be intracortical probe or penetrating shanks indicated generally at 18 having multielectrode sites (not shown). In one exemplary case, each shank 18 has eight iridium sites to monitor and control the neural activity, thereby providing a two-dimensional array of 64 microelectrodes over eight shanks.

To control the electrical stimulation and recordation and provide other control functionality, each device 10, 12 has a backend integrated circuit 20 that may, for instance, include CMOS circuitry disposed on a silicon substrate. FIGS. 1A and 1B depict the devices 10, 12 before and after bending to implement a low-profile implantation. Specifically, the backend circuitry 20 has been bent at a 90 degree angle via, for instance, a bending jig, to allow the dura membrane to be re-positioned over the device, thereby remaining free of the skull, while still enabling membrane penetration by the shanks 18. In this way, the shanks 18 penetrate into the brain cortex while the backend circuitry 20 lies on top of the cortex.

FIG. 2 depicts an exemplary system 22 in which a number of the intracortical probe devices 10, 12 (FIGS. 1A, 1B) have been assembled on a platform 24. In this case, the devices had been bent at different segments or positions of the connectors 14, 16 to enable the devices 10, 12 to be stacked. To this end, spacers 26 and 28 are disposed on the platform 24 to position or fix the devices 10, 12 appropriately via probe outriggers (or other projections) 30, 32 and corresponding receptacles in the spaces 26 and 28. As a result, the probe shanks 18 protrude through holes in the bottom of the platform 24 in spaced fashion. Further control circuitry may be provided on a chip 34 disposed on the platform 24. The chip 34 may be used for signal processing and controlling different probes. The system 22 may connect to a percutaneous plug (not shown) via a flexible cable 36 that may be constructed in accordance with the techniques described below.

The device 22 presents a low-profile three-dimensional stimulating array suitable for use in the central nervous system. After implantation, the platform sits on the cortical surface while the probe shanks penetrate the target neural tissue.

As a result of the arrangement and assembly shown in FIGS. 1A, 1B and 2, the device 22 may include integrated CMOS circuitry in the backends 20, respectively dedicated to separate probe shanks 18. The CMOS circuitry may include on-chip digital-to-analog conversion functionality (DAC) for current generation and on-chip preamplifier(s) to record neural action potential. In one exemplary case, the probe backends 20 measured 5.7 mm by 4 mm and the shanks 18 were 3.3 mm long and 144 µm wide. Each iridium electrode site had approximate size of 1000 µm$^2$, with adjacent sites spaced 400 µm apart along each shank.

With reference again to FIGS. 1A and 1B, the connectors 14, 16 generally provide the flexibility to enable the device arrangements and probe positioning utilized in the neural applications. The flexibility is provided by a number of low-profile structures having an arrangement of flexible, parallel beams 38 that provide the electrical connections and structural support for the connector 14, 16. The beams 38 are supported by, and anchored to, a number of cross-braces, or spans 40 that run orthogonally to the general direction of the beams 38. The bending of the connectors 14, 16 described above may be guided or assisted via the placement of the device 10, 12 in a bending jig or other apparatus for bending between selected, adjacent braces 40.

The braces 40, which may be formed via deep-boron diffused structures as described below, may provide a number of advantages. First, the braces 40 may work as supporting frames or ribs, making the beams 38, and the resulting interconnect, more robust. For instance, the braces may reduce the chances of two beams 38 contacting each other to create a short. Further, the braces 40 divide the gold beams into several segments that serve as guides with respect to the bending position so that the probes can be bent appropriately according to their location (e.g., the absence of any contact between adjacent beams). Still further, these braces 40 also increase the contact area and enhance adhesion between the various layers and materials of the connector (e.g., silicon, Au and parylene). In this way, the braces 40 help prevent the peeling off, or other separation, of the encapsulating and/or insulating layer(s) of the connector from the remainder of the beam 38.

The beams 38 are generally coated with a polymer in accordance with the techniques disclosed herein to help facilitate the bending and improve the flexibility and strength of the connectors 14, 16. The polymer coatings also insulate and encapsulate the connectors 14, 16, thereby supporting the electrical connection functionality as well. Regardless of whether the connectors provide electrical connections, the encapsulation provided by the polymer coatings may also be useful in extending the lifetime of devices implanted or otherwise disposed in environments where fluids and other substances could otherwise degrade the connectors over time.

Figure 3C:
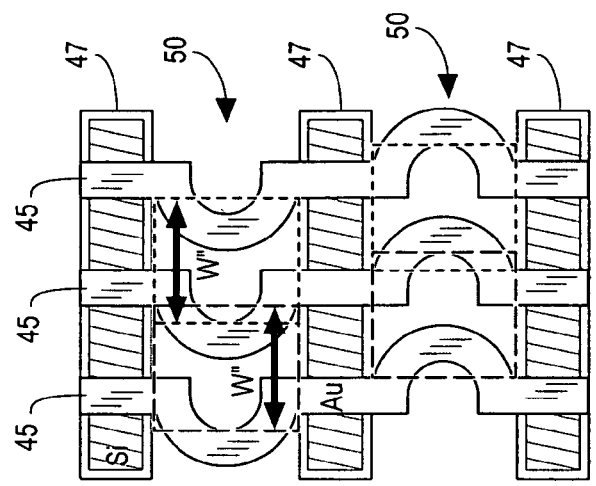
FIGS. 3A-3C are partial, schematic representations of alternative polymer-coated connectors in accordance with another aspect of the disclosure.
Figure 3B:
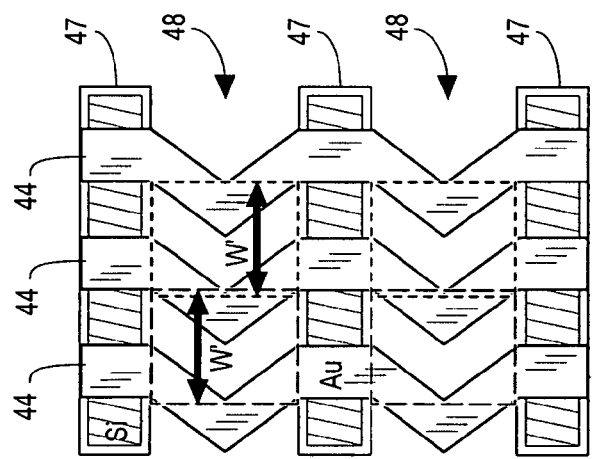
Figure 3A:
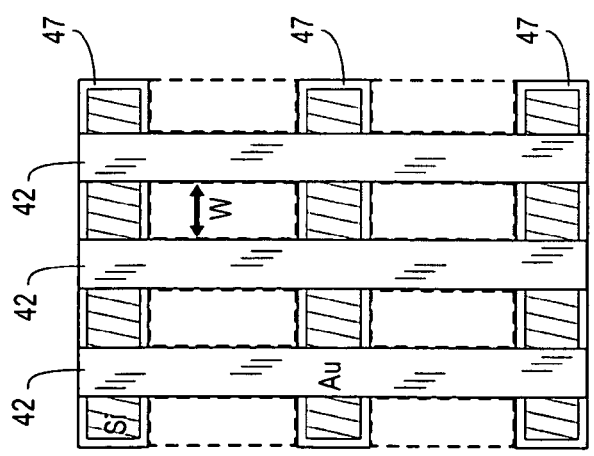

Turning to FIGS. 3A-3C, a number of exemplary connector arrangements configured and constructed in accordance with the disclosed techniques are shown. As a general matter, each connector arrangement includes multiple beams, as described above. In some cases, each beam may be formed via electroplated gold, or some other conductive or flexible metal or other material (e.g., polysilicon). Generally speaking, the materials used in the interior of the connectors may be selected to suit the particular application at hand, and may be driven by considerations of electrical and/or mechanical functionality. In one exemplary embodiment, each beam is approximately 20 µm wide and about 3 to about 5 µm thick. In embodiments having cross-braces, each beam segment between adjacent braces may be, for instance, about 50 µm. The total length of each beam is also application dependent, but may be determined, for instance, by the number of probes in the array so that the backends of the assembled devices can be stacked upon one another as shown in FIG. 2.

When gold is used, the beams can be easily bent at right (or other sharp) angles while maintaining contact resistances less than about 0.05Ω. However, materials that may be used other than (or in addition to) gold (e.g., aluminum) also exhibit suitable flexibility and contact resistance.

As described in detail below, a polymer, such as Parylene C, has been used to encapsulate the beams. Parylene C and other polymers have a number of advantages, including a high electrical resistivity, biocompatibility, low Young's modulus (2-5 GPa), moisture/gas resistance, and deposition conformity. In some cases, the polymer may be deposited in multiple layers to form a sandwich structure to encapsulate the beam. In any case, one or more polymer layers help provide an insulated flexible interconnection or other connection between device structures, such as control circuitry (e.g., a silicon backend) and one or more microstructures (e.g., a microelectrode array).

In accordance with one aspect of the disclosure, the alternative exemplary beam configurations shown in FIGS. 3A-3C are directed to supporting the disclosed fabrication technique. Generally speaking, the beam configuration may be configured to accelerate device release, thereby helping the polymer layers to survive a subsequent etching step, as described below. In this way, the beam configuration supports the integration of the polymer encapsulation layer(s) with the semiconductor structures at the wafer level, thereby enabling batch fabrication.

FIG. 3A shows two connector segments having straight beams 42 arranged in parallel to have a spacing W, while FIGS. 3B and 3C have connector segments with non-straight, or serpentine beams 44 and 46 that present effective spacings W' and W", respectively. More specifically, the connector segments of FIGS. 3B and 3C include beams with multiple serpentine-shaped regions indicated generally at 48, 50, respectively. In this way, each connector segment (or collection of segments) may include beam regions, sections or portions that alternate or otherwise switch between straight and serpentine configurations, but in any event remain separated by effectively parallel spacing, as shown.

As described below, the parallel spacing allows etchant solution to work from the top side of the wafer toward the bottom by proceeding through the spacing formed between the beams 42, 44 or 46 (and any crossing braces or ribs 47) during the device release step. The serpentine-shaped beam regions shown in FIGS. 3B and 3C may be used in some embodiments to expedite silicon bulk etching from the top side so as to minimize the time taken to release the silicon probes (or other microstructure(s)) from the semiconductor substrate (i.e., wafer). As shown via the arrows in FIG. 4A directed at the (111) planes of the semiconductor substrate, typical semiconductor etchant solutions exhibit highly orientation-dependant (i.e., anisotropic) etch characteristics. In silicon, for instance, the (111) planes, with more tightly bonded atoms in the crystal lattice, etch significantly slower than the (100) or (110) planes. As a result, topside anisotropic etching of the underlying semiconductor substrate (or wafer) 52 will nearly stop at the meeting of (111) planes, starting from the opposite edges of the mask formed by the beams 42 and forming a self-limiting V-groove indicated generally at 54 with 54.7° angles to the wafer plane. The depth of the groove (d) is determined by the following relationship, where W is the width between the opposite edges of the beam masks.

$$d = \frac{W}{2\tan(54.7°)}$$

Figure 4B:
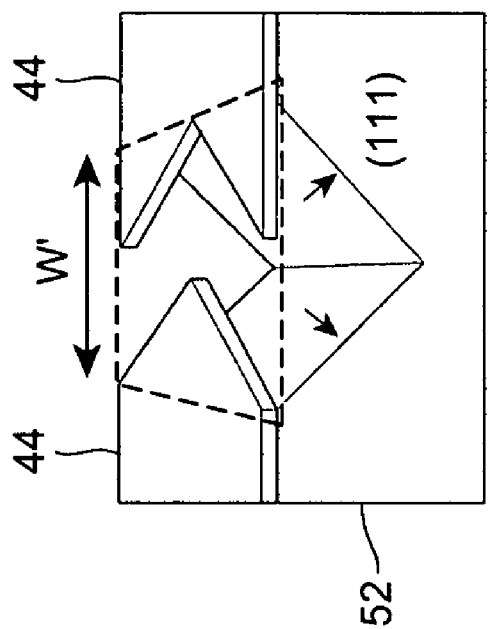
FIGS. 4A and 4B are partial, sectional representations of the alternative connectors shown in FIGS. 3A and 3B at a point during fabrication to illustrate device release in accordance with one aspect of the disclosure.

The silicon under the beams remains intact until the bottom side etch hits the groove 54. But if the opening W' in the beam mask has convex corners or portions as shown in FIG. 4B, the (111) plane generated from that edge will be quickly etched away and etching will only slow down at the (111) plane initiated at the concave edges of the mask. As a result, the effective opening W' is larger than nominal beam spacing (as shown by the overlapping, dashed outlines), thereby leading to a larger topside etch depth, d. In this way, the amount of time that the polymer coatings on the beams are immersed in the etchant solution is decreased.

The zigzag-shaped, saw-tooth, or jagged regions of the beams 44 of FIG. 3B constitute only one exemplary serpentine-shaped configuration for expediting the device release. The semicircle-shaped regions of the beams 46 of FIG. 3C present a further exemplary configuration. Other serpentine, winding or curving shapes are also suitable.

Figure 4A:
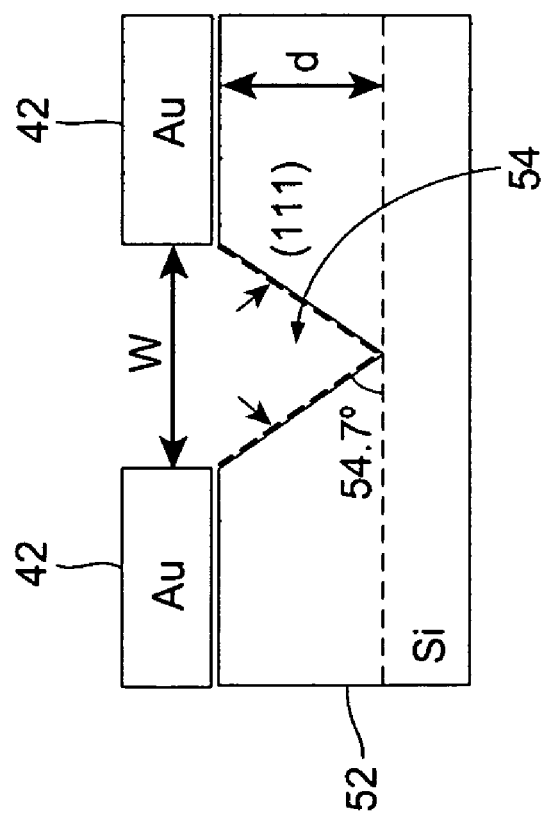

In some cases, without one or more serpentine-shaped regions in the connector, entirely straight beams as shown in FIG. 3A may cause problems during etch release. For example, if the overall dimensions of the connector are particularly wide, then the etchant solution may not reach the interior portions of the connector for quite some time. Otherwise, the beams tend to mask the topside etching and form groove arrays as shown in FIG. 4A.

In some embodiments, the serpentine-, or zigzag-shaped beams are designed so that the resultant grooves initiated from the neighboring opening between the beams overlap with each other. In FIGS. 3B and 3C, this overlap can be seen in the overlapping dashed outlines marked by the spacing distances, W' and W", respectively. As a consequence, the topside etching proceeds rapidly to undercut the beams as if there are no mask layers on top of the semiconductor substrate. For the same reason, instead of continuous polymer films covering the whole interconnection region, the polymer layer is designed to coat each beam separately, i.e., individually, with sufficient space in between to enable and enhance topside etching.

FIGS. 5A-5K depict an exemplary fabrication sequence for the connector 14 and other device components shown in FIG. 1A. The connector 14 has been simplified for purposes of ease in illustration, as, for example, the braces 40 are not shown. But each brace 40 may be fabricated using the same process steps utilized to create the other semiconductor device components described below. Also, the device components associated with the backend circuitry 20 are schematically represented as a semiconductor island having only a pair of contents, with the understanding that the actual device may include far more complex structures, including CMOS and other circuitry for controlling the microelectrode array 18. More generally, the following fabrication sequence and accompanying process parameters are presented with the understanding that the details are exemplary in nature, and that the parameters, dimensions and other details may differ from those set forth below for different applications, contexts, devices, etc.

With reference now to FIG. 5A, the process may begin with a p-type <100>-oriented silicon wafer or substrate 56, a thermal oxide layer 58 is grown and patterned as the mask for a deep boron diffusion. A p++ etch stop 60 having a thickness of about 10 to about 14 μm may be formed after about 8 to about 12 hours of boron diffusion and drive-in at a temperature of about 1100 to about 1200 degrees Celsius. Alternative etch stop thicknesses ranging from about 1 μm to about 16 μm may be obtained with different temperature/time parameters for the diffusion, and/or different energy/dose parameters for the implantation. If a thinner etch stop is required for structures such as silicon ribbon cables, an additional shallow boron diffusion may be performed for about 45 minutes (at similar temperatures) leaving about 3 to about 5 μm boron depth in the target area.

After formation of the etch stop regions, films 61, 62 and 63 of $SiO_2$, $Si_3N_4$, $SiO_2$, respectively, are then deposited as a bottom dielectric to isolate the conducting silicon substrate 56, as shown in FIG. 5B. The composite dielectric stack may be composed of about 3000 Å bottom $SiO_2$, about 1500 Å $Si_3N_4$ and about 3000 Å top $SiO_2$.

Figure 5C:
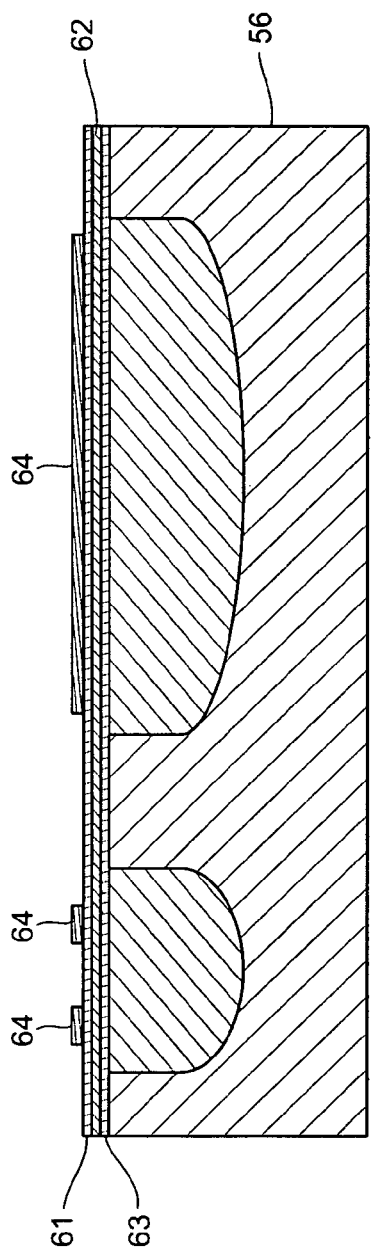
Figure 5D:
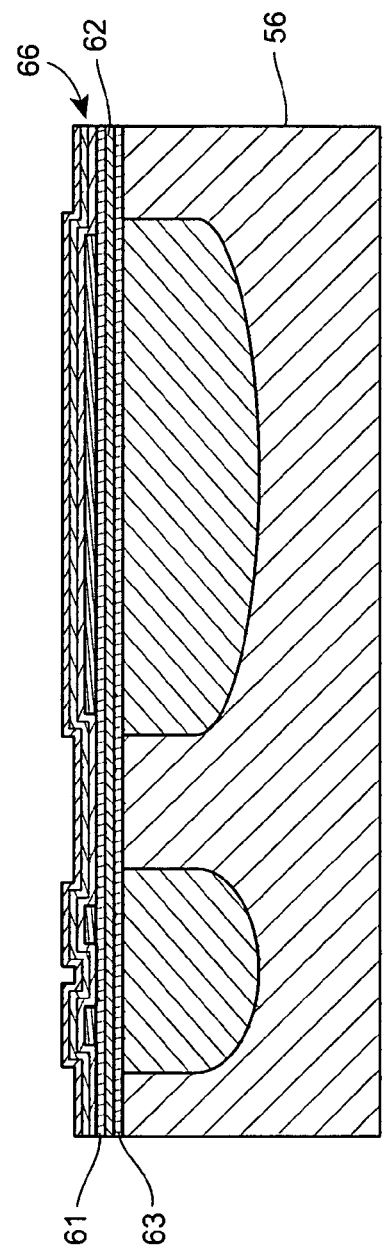

As shown in FIGS. 5C and 5D, polysilicon interconnects 64 are then deposited, doped with phosphorus, and patterned, followed by another LPCVD $SiO_2$, $Si_3N_4$, $SiO_2$ stack indicated generally at 66. The dielectric stack 66 may have the same thicknesses as the previous dielectric stack. These dielectric stacks not only serve as encapsulation layers, they may also play an important role in stress compensation. A thicker silicon nitride layer usually leads to more tight curvature due to tensile stress. Thus, as a general matter, the thickness of the dielectric films may be adjusted for stress compensation and/or to control stress-induced curvature.

In alternative embodiments, a different conductive material than polysilicon may be used for the interconnect layer 64. For instance, metal materials such as aluminum, gold and platinum can also be used for this purpose. Alternatively or additionally, the interconnect layer 64 may be used to connect between the two or more p++ etch stop regions, rather than be used within each device structure (or island), as shown.

Turning to FIG. 5E, contacts indicated generally at 68 are then opened in the top dielectric stack 66 to expose the polysilicon 64 underneath. As shown in FIG. 5F, different contacts 68 may have different conductive materials, resulting in multiple depositions. In this exemplary case, iridium is then sputtered and lifted-off for an electrode site 70, with titanium used underneath to enhance adhesion. Gold is sputtered and patterned for a bonding pad(s) 72 with chromium underneath for adhesion. Again, other metals may be used in addition to, or as alternatives for, those identified. For example, platinum may be used in place of iridium in some cases, but for neural (and other biological) applications, the electrode sites 70 typically have good charge delivery capability to stimulate the implanted neural tissue and record the neural action potential. Of course, in some applications, this step can be skipped if the microstructure does not have electrode sites. In some cases, platinum may be used instead of gold, with titanium for adhesion. Alternatively or additionally, gold/chromium may be put in all the contact recesses to keep the exposed polysilicon interconnects from process contamination and/or to minimize the contact resistance. In alternative embodiments, one or more of these metal sputtering steps may be performed immediately before probe release.

Figure 5G:
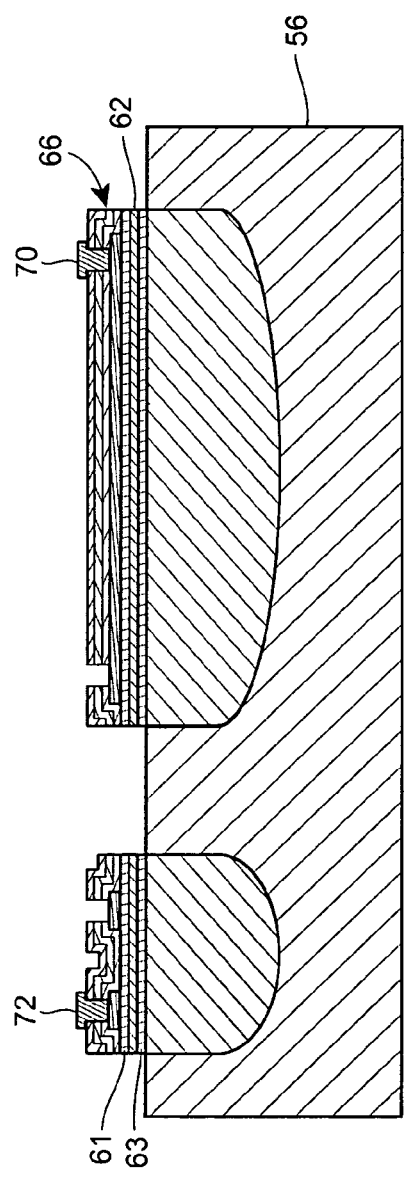

FIG. 5G shows the removal of the field dielectric regions via either RIE dry etching or wet etching, as desired. The field dielectric regions typically refer to the locations where the dielectric layers are not needed for encapsulation. For some applications, like cochlear devices, the dielectric layers are retained between the separated p++ doped regions. The field dielectric layers also expose the silicon underneath for final release.

Figure 5H:
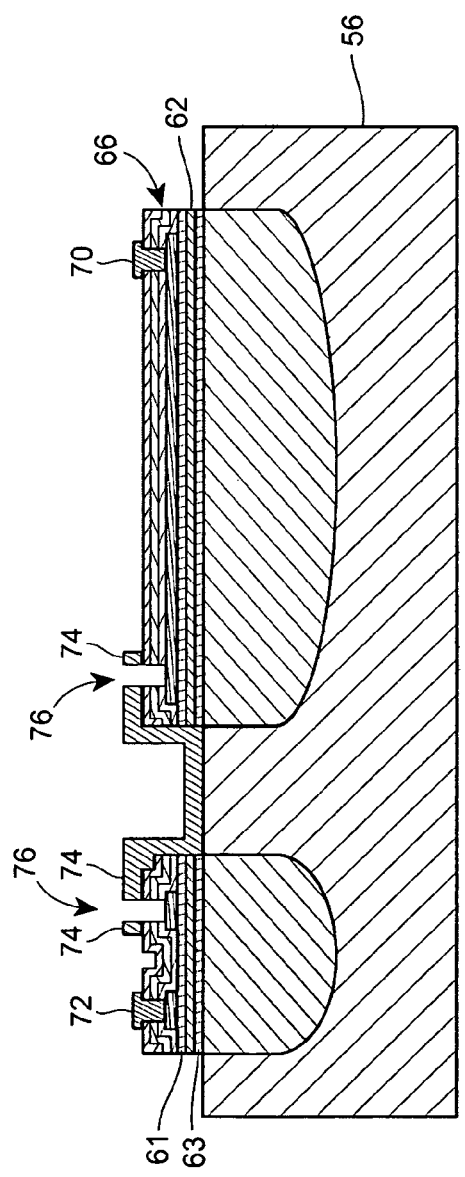

Next, as shown in FIG. 5H, a bottom polymer film 74 is deposited and patterned. In some embodiments, parylene C may be deposited by vapor-phase deposition and polymerization of para-x-xylene, and patterned with $O_2$ plasma dry etching with a photoresist or metal mask. For other suitable polymers, such as BCB or Ctop, a combinational recipe $O_2/CF_4/SF_6$ gas is used, and sometimes Argon (Ar) is introduced to enhance plasma bombardment. In other cases, photo-definable polymers, such as SU-8, Cyclotene, polyimide and PDMS, may be used, through convenient developing and patterning. In this and any other polymer deposition steps, adhesion promotion chemicals well known to those skilled in the art and traditionally added during the deposition process may be used.

Contacts indicated generally at 76 are opened at the same time as polymer patterning. $O_2$ plasma dry etching may be used.

In some cases, the polymer layer 74 may be about 2 µm thick. In some cases (e.g., parylene), the polymer layer 74 is then treated with an $O_2$ plasma to enhance adhesion. In some cases, the polymer layer 74 is subjected to an elevated temperature to, for instance, the glass transition point so that the polymer can reflow and improve chemical stability of the layer 74 to, for instance, eliminate any pinholes and/or other defects.

In alternative embodiments, the polymer layer 74 (and any subsequent polymer layers) may cover further portions of the device structures. For instance, the polymer coating may run the length of the probe shank, covering much, if not all, of the device structure with the exception of the electrode site. The polymer coating may then be patterned, as desired (e.g., to open an electrode, contact or other portion of the device structure). Similarly, the device structure at the other end of the connector may also be encapsulated by the polymer layer 74. In this way, the benefits of polymer coatings (e.g., strength, encapsulation, etc.) are not limited to the connector or cable, but rather may be extended to the device structure(s) to any desired extent. Such extended polymer coating is made possible by the integrated nature of the fabrication process, inasmuch as the polymer layers are deposited during fabrication of the device structures at the wafer level.

Figure 5I:
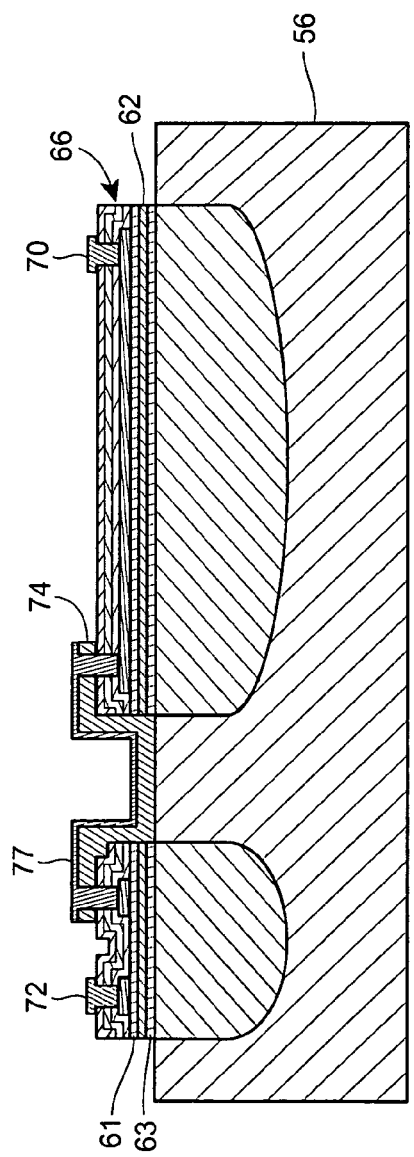

Turning to FIG. 5I, a metal beam 77 is then formed on top of the polymer layer 74. The metal beam 77 may include about 1000 Å to about 5000 Å of gold, which may be sputtered or E-beam evaporated with chromium underneath for adhesion. A chromium-gold seed layer may also be deposited. In any case, the metal beam 77 is then patterned to form the beam shapes described above. If thicker metal beams (e.g., about 6-10 µm) are needed, additional gold may be electroplated on top of the sputtered gold seed. Alternatively or additionally, nickel, aluminum, platinum, and copper can be used. As described above, the beam 77 may also be based on non-metal conductive layers, such as polysilicon. The bonding pads 72 described above may be also done in this step if the same material is used. But generally speaking, this step may be directed to forming the gold beams between the probe backend and shanks and the beam leads on the probe outriggers of the device described above in connection with FIGS. 1A and 1B.

Figure 5J:
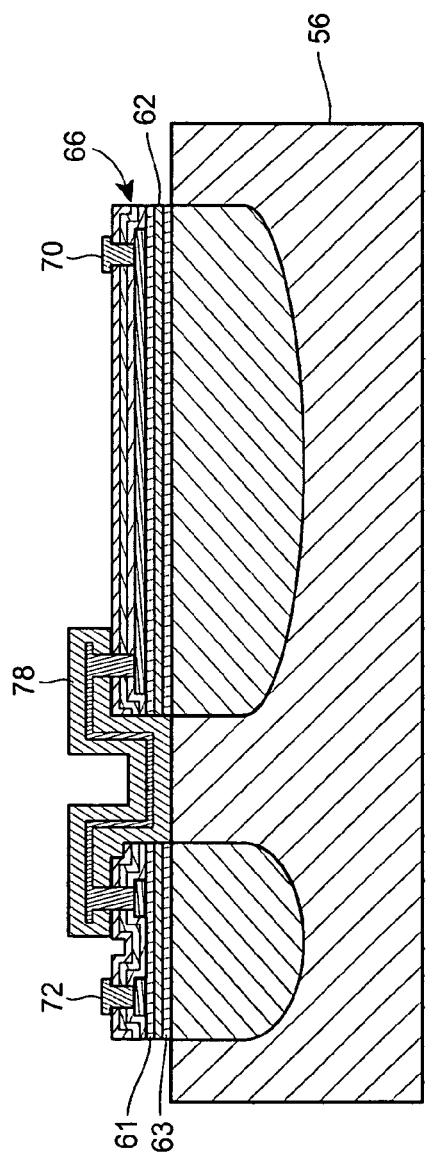
Figure 5K:
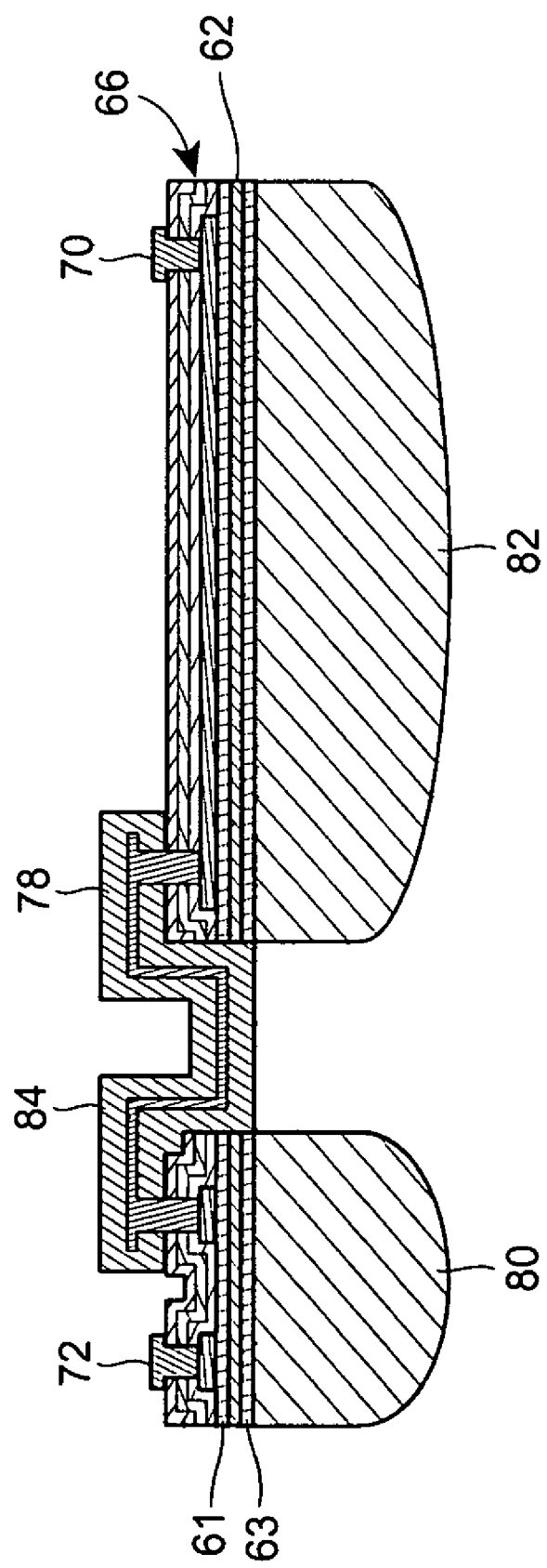

As shown in FIG. 5J, another polymer layer 78 of, for instance, parylene C, is deposited, patterned, and treated in $O_2$ plasma. The polymer layer 78 completes the encapsulation of the gold beams 77 (and, therefore, the connector 14 of FIG. 1A).

After the wafer is thinned from the backside to about 180 to about 200 µm thick in HF-Nitric-Acetic (HNA) solution, with the topside of wafer protected with wax or photoresist, the wafer is etched in a silicon etchant solution (e.g., TMAH) at about 80 degrees Celsius until the device structures (e.g., probes) are released and separated from the wafer. Exemplary released device structures 80 and 82 are shown as two islands connected via a polymer-encapsulated connector 84 in FIG. 5K.

In some cases, such as those involving SOI (silicon-on-insulator) substrates, such backside thinning is not necessary, and a dry etching step may be used in combination with additional or alternative wet etching stops, such as dielectric layers, to release the device structures.

In the final steps, the released structures may be soaked in hot water and then cleaned in acetone and isopropanol (IPA).

The foregoing fabrication sequence is set forth with the understanding that some steps may be performed in different orders other than that described above and shown in the drawing figures, as will be appreciated by those skilled in the art.

The exemplary process described above involves 13 masks, but can be extended to fabricate active probes (rather than the passive ones described above). In alternative cases, a p-type <100>-oriented wafer with a 15 μm thick n-type epi layer may be used to integrate CMOS fabrication with the probe micromachining process. A p-well implant is introduced before the deep boron diffusion to form the substrate for the NMOS transistors. After boron diffusion and lower dielectric deposition, a standard CMOS process may then be executed through aluminum metallization. Low temperature oxide (LTO) is used instead of LPCVD $SiO_2/Si_3N_4/SiO_2$ as the top dielectric layer to protect the aluminum underneath. The following steps may then remain the same. The etching time in TMAH release may be shorter than that for the passive process to protect the circuit area from undercut. The active process involves 20 masks in total.

A number of different polymers and etchant solutions are suitable for use in the above-described fabrication technique. Generally speaking, however, the time taken during the device release etching step (i.e., while the polymer layer is immersed in the etchant solution), is minimized via the top-side etching and backside thinning described above. Taken separately or together, these techniques help arrive at etching times shorted than about 6 hours, and also allow the etching temperature to be relatively low, as described below. The lower temperature (and the resultant slower etch rate) may be tolerated because it helps protect the polymer coating. As described above, the polymer layers may also be protected by curing and treatment after patterning, as well as the semiconductor braces (or ribs) disposed along the dangling polymer beams. As described below in connection with FIG. 6, the polymer layer(s) are also helped via recesses that act as anchors.

In some embodiments, the etchant includes TMAH. One exemplary TMAH etchant recipe contains 1 liter 10 wt. % TMAH solution, 5 g ammonium persulfate $(NH_4)_2S_2O_8$ oxidant additive, and 15 g dissolved silicon powder. Using that recipe, polymer layers of BCB, parylene C, and Cytop all survived one hour etching in TMAH at temperatures ranging from about 80 C through about 95 C. These polymer layers did not exhibit any partial or full peeling, swelling, dissolution or contamination throughout the foregoing range of etching temperatures. With TMAH, the etchant temperature could go as low as 60 degrees Celsius without adversely affecting the time until device release.

Two other commonly used silicon anisotropic etchant solutions are EDP and KOH. EDP has been traditionally used in the fabrication of neural probes due to its high selectivity of deep boron-doped silicon over bulk silicon. One exemplary EDP etchant solution contains 144 ml Dl-H2O, 144 g Catechol, 2.7 g Pyrazine and 450 ml Ethylenediamene. With this recipe, parylene C and Cytop survived one hour etching at temperatures from about 80 C through about 95 C. BCB layers also survived a one-hour etch in EDP at about the low end of the temperature range, e.g., 80 C. While KOH is more aggressive than the other two solutions, an exemplary recipe containing 44% KOH and 56% $H_2O$ with IPA to keep the solution at constant level still allowed a Cytop coated silicon sample to maintain robust adhesion and chemical stability throughout etching at temperatures from about 80 C through about 95 C. This polymer layer did not exhibit any partial or full peeling, swelling, dissolution or contamination.

Figure 6:
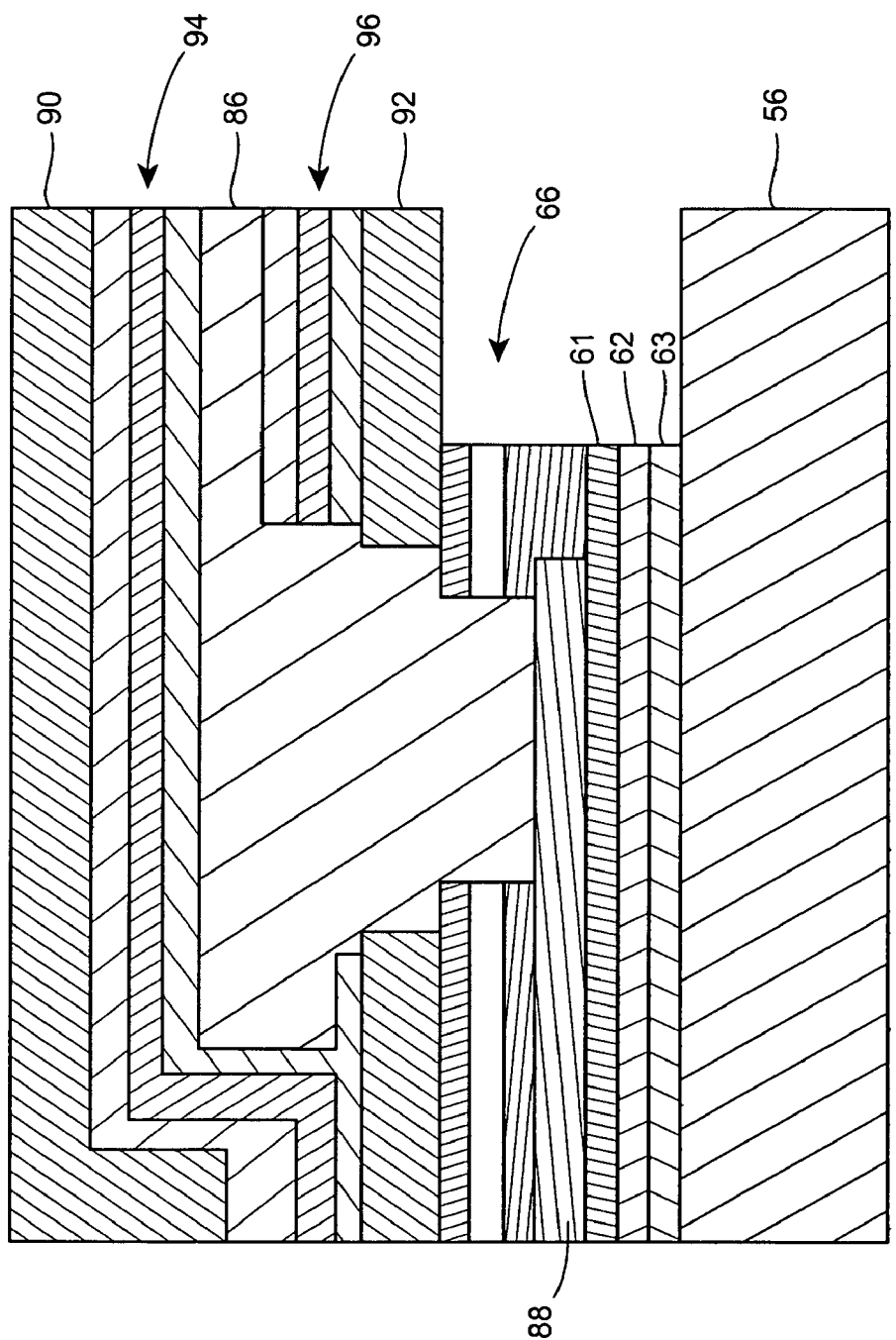
FIG. 6 is a sectional representation of a portion of an exemplary device having a polymer-coated and dielectric-encapsulated interconnect layer in accordance with one embodiment.

FIG. 6 illustrates an embodiment where the device includes an encapsulated interconnect 86 in, for instance, a beam of a connector, contacting a conductive layer 88, of one of the device structures to which the connector is coupled. This embodiment differs from those described above in that the interconnect 86 is encapsulated by one or more layers in addition to top and bottom polymer layers 90 and 92, respectively. Such additional encapsulation may be useful in cases where the interconnect 86 includes a non-biocompatible material (e.g., aluminum), thereby warranting the additional protection. Other suitable cases may involve extended implants, such that, over time, the polymer layers 90, 92 may not be sufficient.

In the exemplary embodiment of FIG. 6, the additional encapsulation is provided by a pair of dielectric stacks indicated generally at 94 and 96. The dielectric stacks 94 and 96 are disposed inside of the polymer layers 90, 92, and may involve materials and thicknesses similar to those described above in connection with the other dielectric stacks involved with the disclosed devices (e.g., the dielectric stack 66, or the layers 61-63).

FIG. 6 also shows how mechanically anchoring the polymer layers 90, 92 on a silicon substrate helps to improve the adhesion between polymer and the device structures, as well as eliminate polymer delamination even when exposed to attacking wet etchant such as TMAH. The beams (or interconnects) 86 connect to the conductive polysilicon lines 88 through contacts opened in silicon dioxide/silicon nitride/silicon dioxide dielectric stack 96 and the bottom polymer layer 92. These contacts automatically form embedded trenches that anchor the polymer film inside the underlying structures. The adhesion between polymer and silicon (i.e., polysilicon) is further enhanced by the adhesion between gold and silicon (polysilicon) and by the gold beams running inside the parylene film 90, 92.

Described above are micro-devices having conductive beams (e.g., Au beams) coated conformally with polymer layer(s), such as parylene strips. In some cases, silicon braces may also be included and coated by the polymer layer(s). The polymer films survive subsequent wet etching without peeling-off or noticeable pinholes, and the silicon underneath the masks created by, for instance, the Au/parylene structures, is etched faster than the silicon in the other device regions (e.g., the microelectrode shanks). The coated beams can be bent easily with little more stress than for bare Au beams. The resulting low-profile structure provides complete electrical isolation for the conducting (e.g., Au) beams along with increased mechanical strength for the probes.

Figure 7:
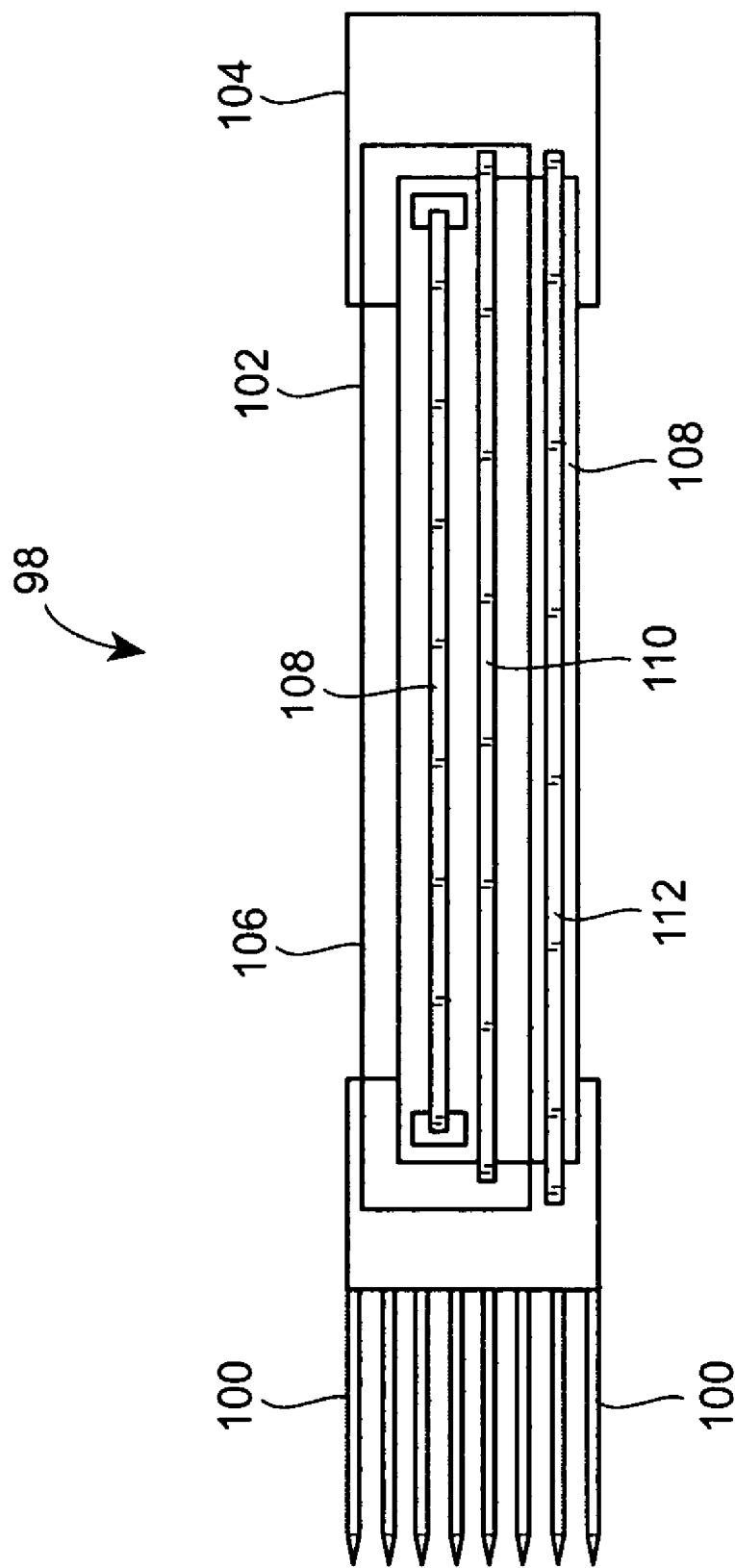
FIG. 7 is a schematic representation of an exemplary device having a flexible, polymer-coated cable with a number of interconnects in accordance with one embodiment.
Figure 8:
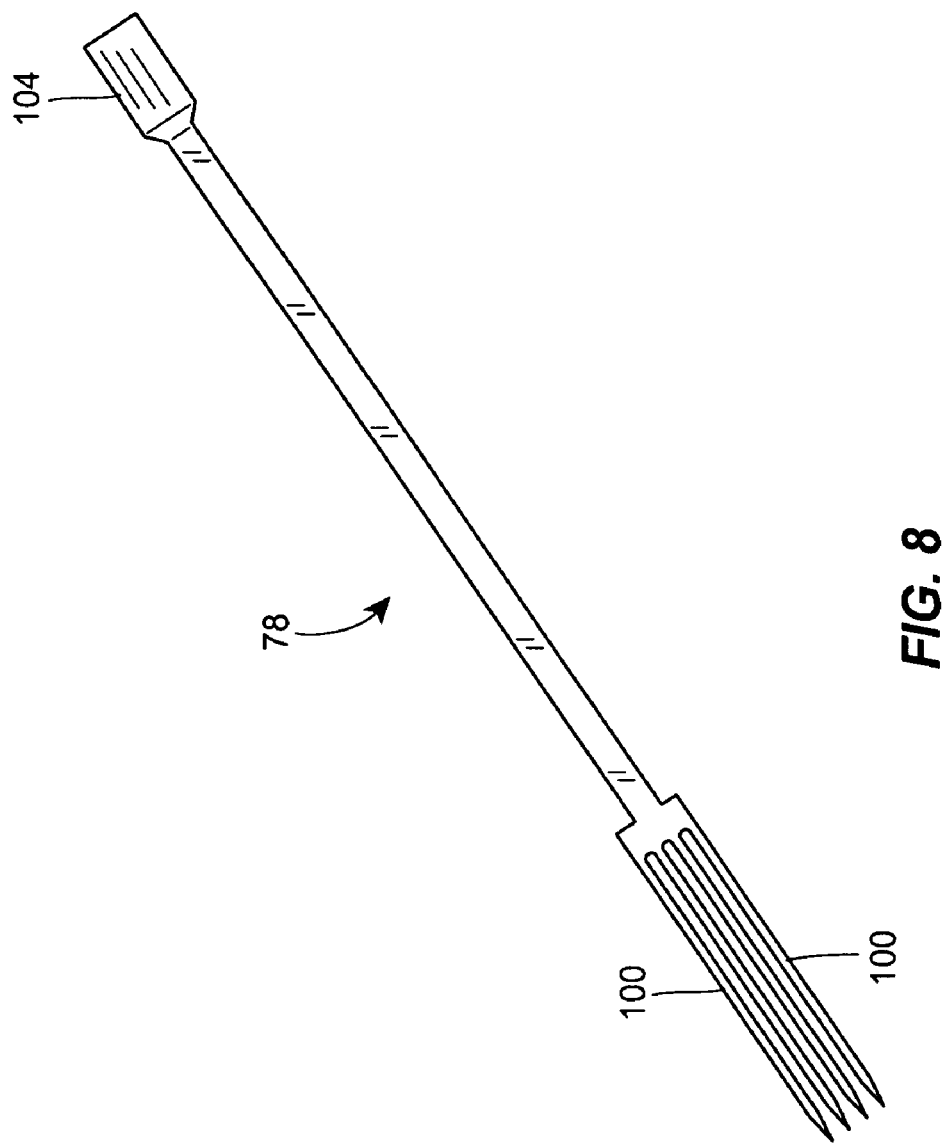
FIG. 8 is a photographic representation of an exemplary device having a flexible, polymer-coated cable similar to the schematic representation of FIG. 7; and, FIG. 9 is a schematic representation of an exemplary device having multiple device structures connected via polymer cables in accordance with one embodiment.

These design principles may be extended to support the fabrication of other devices in addition to the intracortical probes described above. For example, FIGS. 7 and 8 depict schematic and photographic representations of an exemplary probe device indicated generally at 98 having a number of electrode sites on probe shanks 100 disposed at the end of a flexible polymer cable 102. The cable 102 may provide a flexible interconnection between the silicon probes to an external control unit (not shown) via a small device structure 104 at the other end of the cable 102. The structure 104 may include a number of contact pads (not shown) to facilitate the connections. The cable 102 is shown in FIG. 7 with top and bottom polymer layers 106 and 108 for encapsulation of interconnect beams 108 and 110, and for mechanical support of a mechanical beam 112.

Given the size and shape of the device 98, a very large number of these cable-based probes could be fabricated sideby-side at the wafer level utilizing the techniques described above. After the device release step, the device 98 becomes a stand-alone structure, as shown in FIG. 8, that can be easily coupled to further circuitry or device components, such as a percutaneous plug. Once the structures are released from the silicon substrate, the polymer cable can be extremely flexible, such that the photograph of FIG. 8 shows the device 98 after straightening.

Figure 9:
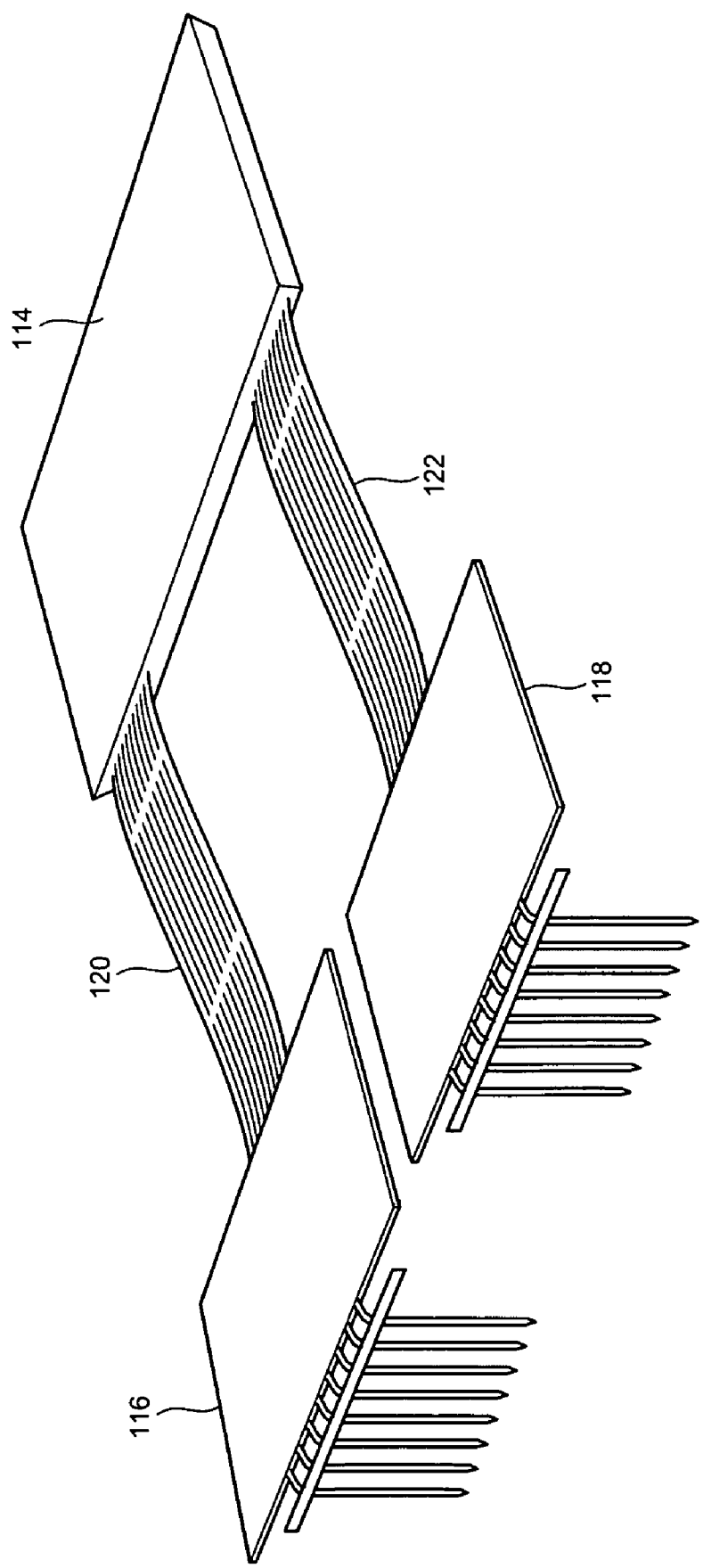

For intracortical neural applications, cables fabricated in accordance with the disclosed techniques may be approximately 1-2 cm long, or longer. They can be easily bent and twisted with minimal invasion and tethering to the neural tissue. In other embodiments, any number of cables may be fabricated, in integral fashion, as part of a system having multiple device structures. As shown in FIG. 9, a single control unit 114 may be coupled to a number of device structures 116, 118 via dedicated cables 120, 122, respectively. Each device structure 116, 118 may correspond with a separate microelectrode probe device as shown.

In the exemplary embodiments of FIGS. 7-9, the polymer layer on the cable may be extended to cover the device structures to any desired extent, such that only electrode sites remain exposed. This broader, more comprehensive encapsulation provides good biocompatible package for the device and system, improves the buckling strength during insertion, and prevents the probe from breaking into pieces during implant and operation.

In accordance with the exemplary embodiments described above, the disclosed integrated silicon/polymer process may be utilized in connection with low-profile three-dimensional microelectrode arrays featuring Au interconnection beams encapsulated conformally with parylene and other polymers, such as SU-8 and Cytop. In other embodiments, it is used successfully to fabricate silicon probes with integrated flexible polymer cables for interfacial connections. The disclosed process may also be used to develop shatter-proof probes for safe implant, or be used for cochlear implants to facilitate insertion into the cochlear channel and integrate a backing insertion tool into the probe so that it can be repositioned during operation. The disclosed polymer-based encapsulation techniques may also be useful in the channels, valves and other components of drug delivery probes and other devices.

As a result of the disclosed technique, flexible polymer cables may be used to connect various implanted neural devices with no need of post-process bonding. In addition, biocompatible polymers may be used for device packaging at the wafer level, thereby reducing time consumption relative to packaging individual devices and increasing the lifetime of neural devices.

The disclosed techniques may also find applications in other MEMS devices which have both silicon and polymer materials in fabrication, such as pressure sensors, microfluidic devices, accelerometers or gyroscopes for automotive applications, etc. Flexible polymer interconnecting cables may also provide uniform and reliable mechanical/electrical interconnections between different MEMS devices and ASIC chips to realize fully functional and integrated button-size Microsystems, thereby helping to save time and effort in system integration due to the batch fabrication. The process also provides an easy and fast way to package silicon devices with polymer materials. For example, the disclosed techniques may provide a mechanism for supporting multi-chip module packaging.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method of fabricating a device having a microstructure, the method comprising the steps of:
   defining the microstructure by forming an etch stop in a semiconductor substrate;
   forming a connector on the semiconductor substrate;
   coating the connector with a polymer layer; and,
   immersing the semiconductor substrate and the coated connector in a wet etchant solution to release the coated connector from the semiconductor substrate and to release the microstructure from the semiconductor substrate in accordance with the etch stop such that the microstructure remains coupled to a further element of the device via the coated connector.

2. The method of claim 1, wherein the connector forming step comprises depositing a conductive layer such that the connector comprises an interconnect between the microstructure and the further element of the device.

3. The method of claim 2, wherein the conductive layer comprises gold.

4. The method of claim 2, wherein the conductive layer comprises aluminum, and wherein the method further comprises the step of encapsulating the conductive layer with one or more dielectric layers before the coating step.

5. The method of claim 1, wherein the forming step comprises the step of defining a plurality of connectors, each of which comprises a serpentine-shaped region, and between each of which the etchant solution flows during the immersing step.

6. The method of claim 1, further comprising the step of defining a brace in the semiconductor substrate as an anchor for the polymer layer.

7. The method of claim 1, further comprising the step of encapsulating the connector with one or more dielectric layers before the coating step.

8. The method of claim 1, further comprising the step of thinning the semiconductor substrate before the immersing step via backside etching.

9. The method of claim 1, wherein the coating step comprises the steps of curing and treating the polymer layer before the immersing step.

10. The method of claim 1, wherein the polymer layer comprises a polymer selected from the group consisting of BCB, Parylene C, and Cytop.

11. The method of claim 1, wherein the etchant solution comprises TMAH.

12. The method of claim 11, wherein the etchant solution comprises 10 wt. % TMAH solution and ammonium persulfate.

13. The method of claim 12, wherein the immersing step is performed at a temperature in a range of about 80 degrees Celsius to about 95 degrees Celsius.

14. The method of claim 1, wherein the coating step comprises the steps of depositing the polymer layer on at least a portion of the microstructure, and selectively patterning the polymer layer before the immersing step.

15. A method of fabricating a device having a microstructure, the method comprising the steps of:
    defining the microstructure by forming an etch stop in a semiconductor substrate;
    forming a connector on the semiconductor substrate;
    coating the connector with a polymer layer; and,
    releasing the microstructure from the semiconductor substrate in accordance with the etch stop by wet etching of the semiconductor substrate, such that the microstructure remains coupled to a further element of the device via the coated connector.

16. The method of claim 15, wherein the connector forming step comprises the step of defining a plurality of connectors, each of which comprises a serpentine-shaped region, and between each of which an etchant solution flows during the releasing step.

17. The method of claim 15, further comprising the step of defining a brace in the semiconductor substrate as an anchor for the polymer layer.

18. The method of claim 15, further comprising the step of encapsulating the connector with one or more dielectric layers before the coating step.

19. A method of fabricating a device having a microstructure, the method comprising the steps of:
    defining the microstructure by forming an etch stop in a semiconductor substrate;
    coating the microstructure and the semiconductor substrate with a polymer layer;
    selectively patterning the polymer layer; and,
    releasing the microstructure from the semiconductor substrate in accordance with the etch stop by wet etching of the semiconductor substrate after the polymer layer patterning step, such that the microstructure remains coated with the polymer layer.

20. The method of claim 19, further comprising the step of thinning the semiconductor substrate before the releasing step via backside etching.

21. The method of claim 19, further comprising the steps of curing and treating the polymer layer before the releasing step.

22. The method of claim 19, wherein the polymer layer comprises a polymer selected from the group consisting of BCB, Parylene C, and Cytop.

23. The method of claim 19, wherein the releasing step comprises the step of immersing the semiconductor substrate in an etchant solution comprising TMAH.

24. The method of claim 23, wherein the etchant solution comprises 10 wt. % TMAH solution and ammonium persulfate.

25. The method of claim 23, wherein the immersing step is performed at a temperature in a range of about 80 degrees Celsius to about 95 degrees Celsius.

26. The method of claim 19, wherein the releasing step is performed such that the microstructure remains coupled to a further element of the device via the polymer layer.

27. The method of claim 26, wherein the further element of the device is another microstructure.

* * * * *